(12) United States Patent
Wang et al.

(10) Patent No.: US 8,648,042 B2
(45) Date of Patent: Feb. 11, 2014

(54) PHARMACEUTICAL COMPOSITIONS

(75) Inventors: Chau-Hui Wang, Kaoshiung (TW); Chia-Hung Chen, New Taipei (TW); Jing-Yi Chen, Taipei (TW); Chih-Wei Hsu, Kaoshiung (TW)

(73) Assignee: Taiwan Hopax Chems. Mfg. Co., Ltd., Kaohsiung (TW)

( * ) Notice: Subject to any disclaimer, the term of this patent is extended or adjusted under 35 U.S.C. 154(b) by 0 days.

(21) Appl. No.: 13/483,382

(22) Filed: May 30, 2012

(65) Prior Publication Data

US 2013/0005661 A1     Jan. 3, 2013

Related U.S. Application Data

(60) Provisional application No. 61/493,004, filed on Jun. 3, 2011.

(51) Int. Cl.

| | |
|---|---|
| *A61K 8/00* | (2006.01) |
| *A61K 38/39* | (2006.01) |
| *C07K 7/06* | (2006.01) |
| *C07K 7/08* | (2006.01) |
| *C07K 14/78* | (2006.01) |
| *A61K 47/48* | (2006.01) |
| *A61K 8/65* | (2006.01) |
| *A61L 27/24* | (2006.01) |

(52) U.S. Cl.
USPC ........................................ 514/17.2; 514/1.1

(58) Field of Classification Search
CPC ......... A61K 38/00; A61K 38/39; C07K 7/06; C07K 14/78
USPC ................................................ 514/1.1, 17.2
See application file for complete search history.

(56) References Cited

U.S. PATENT DOCUMENTS 5,591,731 A * 1/1997 Kennedy et al. ............... 514/114
2006/0198786 A1 * 9/2006 Wei et al. ...................... 424/1.69

OTHER PUBLICATIONS

Han, H.-K. "Targeted prodrug design to optimize drug delivery," AAPS Pharmsci. 2(1), Article 6:1-11 (2000).*
Beaumont, et, al "Design of Ester Prodrugs to Enhance Oral Absorption of Poorly Permeable Compounds: Challenges to the Discovery Scientist," Current Drug Metabolism 4:461-485 (2003).*
Muller, Christa E. "Prodrug Approaches for Enhancing the Bioavailability of Drugs with Low Solubility," Chemistry & Biodiversity, vol. 6:2071-2083 (2009).*
Singh, Yashveer et al, "Recent Trends in Targeted Anticancer Prodrug and Conjugate," DesignCurr Med Chem. 15(18):1802-1826 (2008).*
Ettmayer P. et al., "Lessons leared from marketed and investigational prodrugs," J. Med. Chem. 47(10):2393-2404 (2004).*
Testa, B. "Prodrug research: futile or fertile?" Biochemical Pharmacology 68:2097-2106 (2004).*
Kouvaris et al.—"Amifostine: The First Selective-Target and Broad-Spectrum Radioprotector", The Oncologist (2007), vol. 12, pp. 738-747.
Shaw et al.—"Human Pharmacokinetics of WR-2721", Int. J. Radiation Oncology Biol. Phys. (1986), vol. 12, pp. 1501-1504.

* cited by examiner

*Primary Examiner* — Christina Bradley
*Assistant Examiner* — Kristina M Hellman
(74) *Attorney, Agent, or Firm* — Bacon & Thomas, PLLC

(57) ABSTRACT

A pharmaceutical polymer and a method for quenching free radicals is described. The pharmaceutical polymer comprises a glycopeptide covalently bound to an aminothiol moiety. The pharmaceutical polymer and method can be applied before or after the occurrence of radiation exposure.

16 Claims, 4 Drawing Sheets

(1) Control
(2) EcoRI
(3) 20mM $H_2O_2$ +UV 20 mJ/cm$^2$
(4) 4000ug/ml GP
(5) 2000ug/ml Amifostine
(6) 4000ug/ml GP-Amifostine
(7) 4000ug/ml GP + 2000ug/ml Amifostine
(8) 2000ug/ml Amifostine + 2U/ml Alkaline phosphatase
(9) 4000ug/ml GP-Amifostine + 2U/ml Alkaline phosphatase

PHARMACEUTICAL COMPOSITIONS

This application claims priority to U.S. provisional patent application No. 61/493,004, filed on Jun. 3, 2011, which is hereby incorporated by reference in its entirety.

FIELD OF THE INVENTION

The present invention relates to an anti-free radicals pharmaceutical polymer, more specifically, to an anti-free radicals pharmaceutical polymer having an aminothiol moiety.

DESCRIPTION OF THE PRIOR ART

Interest in the pharmacological protection of tissues from radiation effects is longstanding. One very promising radioprotector that has grown out of this effort is Amifostine (MEDIMMUNE™ Oncology, Inc, Gaithersburg, Md.), an organic thiophosphate developed by the United States Army (WR-2721) in the post-World War II era to protect against the possible effects of radioactive fallout. The active metabolite (WR-1065) is a free thiol that is thought to provide an alternative target to DNA for reactive species from alkylating agents and as a scavenger of free radicals yielded by interactions of ionizing radiation and water. In extensive study of the drug, and colleagues concluded that WR-2721 was selectively concentrated in normal tissues but passively absorbed by tumors as a result of differences in vascularity. It protected normal tissues, including esophagus, lung, kidney, liver, bone marrow, immune system, skin, colon, small bowel, salivary gland, oral mucosa, and testis from radiation damage up to a factor of 3; brain and spinal cord, however, were not protected. In addition, there was no evidence that tumors were spared the effects of radiation or chemotherapy.

Amifostine (also known as S-2-(3-aminopropylamino) ethyl dihydrogen phosphorothioate, ethiofos, ETHYOL™, NSC 296961, or WR-2721) originally developed by the Walter Reed Institute of Research was used as an antiradiation agent for military use against x-ray or nuclear radiation encountered during military conflicts. Bulk amifostine along with other aminoalkyl dihydrogen phosphorothioates and preparation methods for the same are disclosed in U.S. Pat. No. 3,892,824, which is incorporated herein as reference.

Amifostine has also been shown to protect normal tissues against several classes of cytotoxic agents including alkylating and organoplatinum agents, anthracyclines, and taxane. Therefore, it promises to have broad applicability as a cytoprotective agent. Amifostine is already approved for use as a radioprotector in the United States on the basis of an international multi-institutional phase III comparative trial that demonstrated a significant reduction in the severity of acute and late xerostomia in patients given Amifostine intravenously before each fraction of radiation therapy.

More recently, a prospective comparative trial was conducted at The University of Texas M. D. Anderson Cancer Center (reported at the 2001 ASCO Meeting, San Francisco Calif., Nov. 12-15, 2001) with the aim of determining whether by reducing the major toxic effects of chemoradiation therapy on critical organs, Amifostine would allow concurrent chemotherapy and radiation therapy to be intensified thereby increasing tumor control and survival in patients with NSCLC. Sixty-two patients were enrolled between 11/98 and 1/01, permitting a minimum follow-up of 12 months and a median follow-up of 24 months. Patient and tumor characteristics were equally distributed between (A) a no Amifostine arm and (B) an Amifostine arm. Median survival times were 20 months in Arm 1 patients and 19 months in Arm 2 patients.

However, systemic administration of amifostine has several disadvantages. Firstly, patients with systemic administration of amifostine may suffer from undesirable side-effects such as nausea, vomiting, emesis and hypotension, as well as flushing or feeling of warmth, chills or feeling of coldness, dizziness, somnolence, hiccups and sneezing. Furthermore, systemic amifostine could also be toxic at high dose. Secondly, amifostine tends to be discharged from a human body within one hour, which therefore fails to effectively perform the desired radioprotection effect.

To sum up, a proper modification of amifostine for providing longer retention time and specific localization in tissues or organs is required in the field for reducing the undesirable side-effects and enhancing the radioprotection effect thereof.

SUMMARY OF THE INVENTION

The present invention provides a pharmaceutical polymer, comprising: a glycopeptide having a polypeptide and at least one glycoside moiety; wherein said at least one glycoside moiety covalently bonds to said polypeptide; and an aminothiol moiety, having at least one amino group; wherein said at least one amino group of said aminothiol moiety covalently bonds to said glycopeptide.

Preferably, said polypeptide has at least one carboxylic acid group.

Preferably, said at least one glycoside moiety covalently bonds to said at least one carboxylic acid group of said polypeptide.

Preferably, said at least one amino group of said aminothiol moiety covalently bonds to said at least one carboxylic acid group of said polypeptide.

Preferably, said polypeptide has at least one subunit comprising a glutamic acid, an aspartic acid or a combination thereof.

Preferably, said polypeptide comprises poly(glutamic acid), poly(aspartic acid), or a combination thereof.

Preferably, said pharmaceutical polymer has a molecular weight of 6,300~12,000 daltons.

Preferably, said at least one glycoside moiety has at least one amino group.

Preferably, said at least one amino group of said at least one glycoside moiety covalently bonds to said at least one carboxylic acid group of said polypeptide.

Preferably, said at least one glycoside moiety comprises chitosan, collagen, chondroitin, hyauraniate, heparin, or a combination thereof.

Preferably, said aminothiol moiety has the following formula (I):

$$(R_1NH(CH_2)_nNH(CH_2)_mSR_2)_x; \qquad (I)$$

wherein said $R_1$ is H, $C_1$-$C_7$ alkyl, $C_2$-$C_7$ alkenyl, $C_2$-$C_7$ alkynyl, $C_5$-$C_7$ aryl, or $C_2$-$C_7$ acyl;
said $R_2$ is H or phosphate group;
n is an integer from 1 to 10;
m is an integer from 1 to 10; and
x is an integer from 1 to 5.

Preferably, said aminothiol moiety is selected from the group consisting of WR-1065, WR-151326, WR151327, WR638, WR3689, WR2822, WR-2529, WR-77913, WR-255591, WR-2823, WR-255709, WR-33278, WR2721 (amifostine), salts, hydrates, active metabolite, prodrug thereof, and a combination thereof.

Preferably, said aminothiol moiety is amifostine.

The present invention also provides a method for quenching free radicals, comprising administering an effective amount of the aforesaid pharmaceutical polymer to a subject.

Preferably, said administering is via oral or intravenous injection.

Preferably, said free radicals result from exposing said subject to radiation.

Preferably, said administering is made before or after said exposing.

Preferably, said radiation is x-ray radiation, nuclear radiation, gamma radiation, alpha radiation, beta radiation or a combination thereof.

Preferably, said effective amount is 100~5,000 mg/m$^2$.

Preferably, said subject is an animal.

Preferably, said animal is human.

Preferably, said polypeptide of said pharmaceutical polymer comprises poly(glutamic acid), poly(aspartic acid), or a combination thereof.

Preferably, said at least one glycoside moiety of said pharmaceutical polymer comprises chitosan, collagen, chondroitin, hyauraniate, heparin, or a combination thereof.

Preferably, said aminothiol moiety has the following formula (I):

$(R_1NH(CH_2)_nNH(CH_2)_mSR_2)_x;$         (I)

wherein said $R_1$ is H, $C_1$-$C_7$ alkyl, $C_2$-$C_7$ alkenyl, $C_2$-$C_7$ alkynyl, $C_5$-$C_7$ aryl, or $C_2$-$C_7$ acyl;

said $R_2$ is H or phosphate group;

n is an integer from 1 to 10;

m is an integer from 1 to 10; and x is an integer from 1 to 5.

Preferably, said aminothiol moiety of said pharmaceutical polymer is amifostine.

The present invention further provides a pharmaceutical composition, comprising: a pharmaceutical polymer according to claim 1; and a pharmaceutical acceptable carrier.

Preferably, said pharmaceutical acceptable carrier comprises glucose, saccharose, lactose, fructose, starch, dextrins, cyclodextrins, polyvinylpyrrolidone, alginic acid, tylose, silicic acid, cellulose, cellulose derivatives, mannitol, sorbitol, calcium carbonate, calcium phosphate, or combination thereof.

DESCRIPTION OF THE PREFERRED EMBODIMENTS

Figure 1:
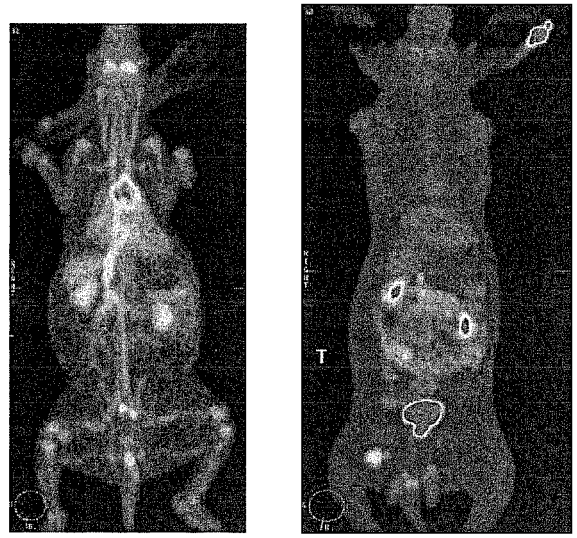
FIG. 1 shows that the in vivo distribution of GP.

What probed into the invention is a pharmaceutical polymer and use of the same. Said pharmaceutical polymer comprises a glycopeptides and an aminothiol moiety. The claimed use of said pharmaceutical polymer is for quenching free radicals.

One of the key concepts of the present invention is to modify an aminothiol pharmaceutical compound by conjugating a glycopeptides. The conjugation can provide advantages of specific localization and prolonged retention time to said aminothiol pharmaceutical compound.

Detail descriptions of the measuring procedures and system will be provided in the following sentences in order to make the invention thoroughly understandable. Obviously, the application of the invention is not confined to specific details familiar to those who are skilled in the art. On the other hand, the common process and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

As mentioned above, the present pharmaceutical polymer comprises a glycopeptide and an aminothiol moiety. Said glycopeptides has a polypeptide and at least one glycoside moiety.

The conjugation between said polypeptide and said at least one glycoside moiety is that said at least one glycoside moiety bonds to said polypeptide via a covalent bond.

Preferably, said polypeptide has at least one carboxylic acid group. Therefore, in a preferred embodiment, said at least one glycoside moiety covalently bonds to said at least one carboxylic acid group of said polypeptide. In another preferred embodiment, said glycoside moiety has at least one amino group; wherein said at least one amino group of said at least one glycoside moiety covalently bonds to said at least one carboxylic acid group of said polypeptide.

In a preferred embodiment, said polypeptide has at least one subunit comprising a glutamic acid, an aspartic acid or a combination thereof. Alternatively, said polypeptide is poly (glutamic acid), poly(aspartic acid), or a combination thereof. In another preferred embodiment, said pharmaceutical polymer has a molecular weight of 6,300~12,000 daltons.

It is benefit to select said glycoside moiety from chitosan, collagen, chondroitin, hyauraniate, heparin, or a combination thereof, because the above-mentioned glycoside moieties are able to provide the properties of specific localization and prolonged retention time to the claimed structure.

Said aminothiol moiety has at least one amino group. The conjugation between said aminothiol moiety and said glycopeptides is that said at least one amino group of said aminothiol moiety covalently bonds to said glycopeptide. In a preferred embodiment, said at least one amino group of said aminothiol moiety covalently bonds to said at least one carboxylic acid group of said polypeptide.

In a preferred embodiment, said aminothiol moiety has the following formula (I):

$(R_1NH(CH_2)_nNH(CH_2)_mSR_2)_x;$         (I)

wherein said $R_1$ is H, $C_1$-$C_7$ alkyl, $C_2$-$C_7$ alkenyl, $C_2$-$C_7$ alkynyl, $C_5$-$C_7$ aryl, or $C_2$-$C_7$ acyl;

said $R_2$ is H or phosphate group;

n is an integer from 1 to 10;

m is an integer from 1 to 10; and x is an integer from 1 to 5.

Examples of said aminothiol moiety include but not limit to WR-1065, WR-151326, WR151327, WR638, WR3689, WR2822, WR-2529, WR-77913, WR-255591, WR-2823, WR-255709, WR-33278, WR2721 (amifostine), salts, hydrates, active metabolite, prodrug thereof, and a combination thereof.

The method of the present invention is for quenching free radicals in vivo. The method comprises administering an effective amount of the aforesaid pharmaceutical polymer to a subject orally or via intravenous injection.

The free radicals may result from exposing said subject to radiation, such as x-ray radiation, nuclear radiation, gamma radiation, alpha radiation, beta radiation or a combination thereof. Besides, said administering can be made before or after said exposing based on doctor's advices.

Said effective amount is between 100 mg/m$^2$~5,000 mg/m$^2$. The preferred effective amount may depend on the physical condition or body weight of the subject concerned as well as the encountered radiation intensity.

Said pharmaceutical polymer can be administered with a pharmaceutically acceptable carrier or any other favorable additives as a pharmaceutical composition. Said carrier or additive shall be no adverse effect on the desired function of said pharmaceutical polymer. The term of "adverse effect" means reducing the ability in quenching free radicals as well as effecting the retention time or uptaking of said pharmaceutical polymer.

The pharmaceutically acceptable carrier may be glucose, saccharose, lactose, fructose, starch, dextrins, cyclodextrins, polyvinylpyrrolidone, alginic acid, tylose, silicic acid, cellulose, cellulose derivatives, mannitol, sorbitol, calcium carbonate, calcium phosphate, or combination thereof. The additive may be a buffer, a preservative, a suspending agent, a thickening agent, a surfactant, an isotonic agent or a combination thereof.

Example 1

GP-Guided Localization

Glycopeptide (GP) as a carrier combining with drug are disclosed in patent application Ser. No. 12/970,026, and it is already known the distribution of GP may include lung, kidney, liver, the inflammatory, red marrow, and tumor regions. Here we used PET (Positron Emission Tomography) scan for detecting the localization of two different contrast agents $^{68}$Ga-GP(left), $^{18}$F-FTG(right) in New Zealand Rabbits injected with VX-2 tumor cells.

Briefly, animals were housed in the University of Texas M.D. Anderson Cancer Center facility. The protocols involving rats and radioisotopes were approved by the M.D. Anderson Animal Use and Care Committee, and Radiation Safety Committee. Female Fischer 344 rats (150-175 g) (Harlan Sprague-Dawley, Inc., Indianapolis, Ind.) were inoculated subcutaneously in the right leg with breast cancer cells (10$^6$ cells/rat) from the breast cell line (known as DMBA-induced breast cancer cell line).

Localization studies of the example were performed on day 14 after inoculation. A group of female Fischer 344 tumor-bearing rats was injected intravenously with $^{68}$Ga-GP(left) or $^{18}$F-FTG(right) through the tail vein. The injected mass was 30 µg per rat. The PET scan is performed at 45 minutes after injection.

FIG. 1 shows the result of PET scan; wherein the distribution of GP includes lung, kidney, liver, the inflammatory, red marrow, and tumor regions. The experimental result confirms GP as a potential candidate for modifying an aminothiol pharmaceutical compound in our following studies.

Example 2

Preparation of the Pharmaceutical Polymer of the Present Invention

The preparation of the pharmaceutical polymer of the present invention is indicated as the following reaction Scheme 1:

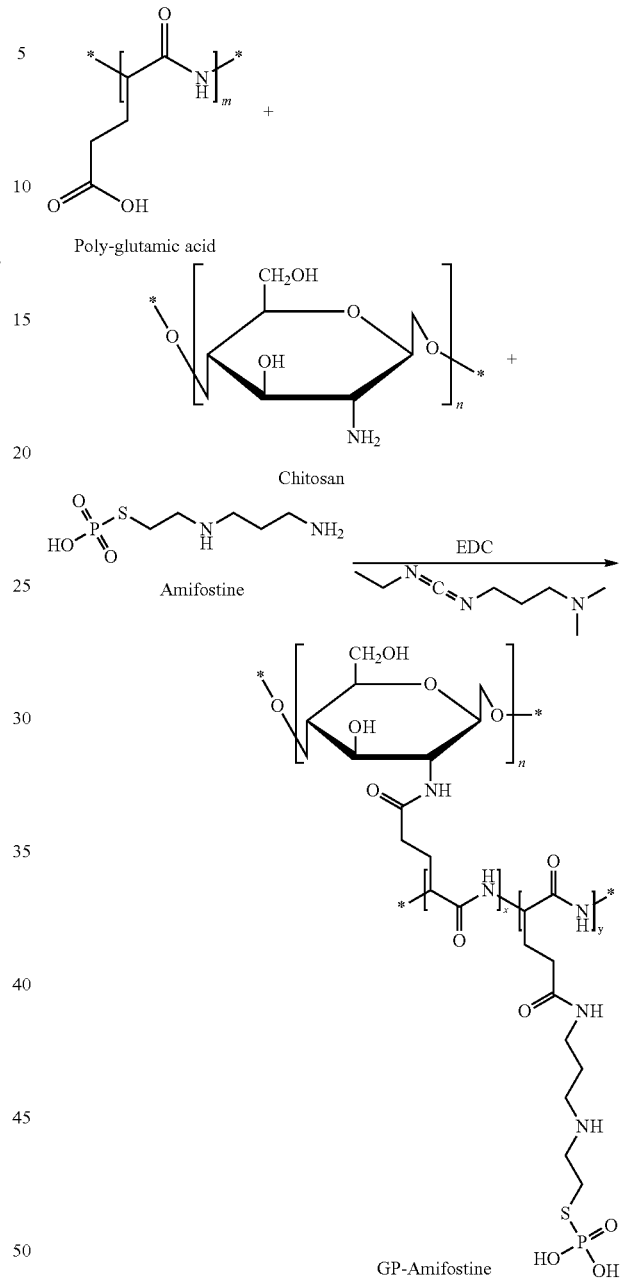

Scheme 1: Synthesis of GP-A

As noted, the polypeptide used in this example was poly-glutamic acid; the glycoside moiety used was chitosan; and the aminothiol moiety used was amifostine or WR1065 (not shown). The synthesis protocol is briefly described as follows:

Obtaining a solution of poly-L-glutamic acid; wherein 0.585 g of poly-L-glutamic acid is dissolved in 25 mL of water. The pH value of said solution of poly-L-glutamic acid is adjusted to about 7.1;

Obtaining a chitosan solution; wherein 0.74 g of chitosan is dissolved in 18 mL of water. The pH value of said chitosan solution is also adjusted to about 7.1;

Mixing 0.743 g of EDC (N-Ethyl-N'-(3-dimethylamino-propyl carbodiimide hydrochloride) with said solution of poly-L-glutamic acid;

Dissolving 0.57 g of amifostine into said solution of poly-L-glutamic acid;

Mixing said chitosan solution with said solution of poly-L-glutamic acid to obtain a mixture and stirring said mixture for 24 hours;

Purifying said mixture by dialysis for two times (molecular weight of the membrane used is 10 k); and Frozen-drying said mixture to obtain a product, which is the pharmaceutical polymer of the present invention in this example. The product is referred to as GP-Amifostine (GP-A) and GP-WR1065, respectively in the following paragraphs or experiments.

Since both free Amifostine and WR-1065 have sulphuric ion and/or phosphate group, whereas GP alone does not have neither of those functional groups, we used ICP (Inductively Coupled Plasma) or EA(Elemental analysis) as a technique to identify the loading rate of GP-A (Amifostine to GP). The loading rate of Amifostine to GP in this example is measured as 1~30 wt %. Besides, the GP-Amifostine made in this example has a molecular weight of 6,300~11,700 daltons, which was various in accordance with the loading rate.

Pure water or co-solvent can be used for the synthesis of GP-Amifostine. Co-solvent is able to increase the production ratio of GP-Amifostine/GP-WR1065 through reducing the hydrolysis of phosphate group within Amifostine.

Example 3

Biodistribution of GP-A of the Present Invention

In this example, we monitored the in vivo localization of GP-A in rats by labeling it with sodium pertechnetate (Na$^{99m}$TcO$_4$) and detecting the same by PET at 0.5 hours, 2 hours, and 4 hours after oral administration.

The experiment is conducted in accordance with Example 1 with slight modification. Animals were housed in the University of Texas M.D. Anderson Cancer Center facility. The protocols involving rats and radioisotopes were approved by the M.D. Anderson Animal Use and Care Committee, and Radiation Safety Committee. Female Fischer 344 rats (150-175 g) (Harlan Sprague-Dawley, Inc., Indianapolis, Ind.) were inoculated subcutaneously in the right leg with breast cancer cells (10$^6$ cells/rat) from the breast cell line (known as DMBA-induced breast cancer cell line).

Biodistribution studies of the example were conducted on day 14 after inoculation. 9 tumor-bearing mice were used and divided into three groups, each group representing a time interval (0.5, 2, and 4 hr, n=3/time point). 20 μCi of $^{99m}$Tc-GP-A was injected via a lateral tail vein. After administration, the mice were sacrificed at certain time point and the selected tissues were excised, weighed and counted for radioactivity with a gamma counter. The distribution of radiotracer in each organ was expressed as percentage of the injected dose per gram of tissue (% ID/g). Tumor/normal tissue count ratios were determined from the corresponding % ID/g values. In statistical analysis, percent of injected dose per gram of tissue weight (% ID/g) and tumor-to-tissue ratios used in biodistribution studies will be presented as means±SD. The results are listed in the following table 1:

TABLE 1

Biodistribution of 99mTc-GP-A in Breast Tumor-Bearing Rats (Count at 100-200 keV window)

| Organ | 0.5 HR | 2 HR | 4 HR |
|---|---|---|---|
| BLOOD | 3.56 ± 0.03 | 1.80 ± 0.08 | 1.12 ± 0.06 |
| HEART | 0.46 ± 0.03 | 0.33 ± 0.04 | 0.23 ± 0.01 |
| LUNG | 1.08 ± 0.05 | 0.64 ± 0.04 | 0.42 ± 0.03 |
| THYROID | 0.15 ± 0.16 | 0.59 ± 0.05 | 0.43 ± 0.01 |
| PANCREAS | 0.27 ± 0.01 | 0.19 ± 0.02 | 0.15 ± 0.02 |
| LIVER | 1.13 ± 0.03 | 1.58 ± 0.07 | 1.85 ± 0.08 |
| SPLEEN | 0.86 ± 0.02 | 1.12 ± 0.08 | 1.34 ± 0.01 |
| KIDNEY | 7.22 ± 0.15 | 10.11 ± 0.55 | 10.33 ± 0.90 |
| STOMACH | 0.22 ± 0.01 | 0.17 ± 0.02 | 0.15 ± 0.02 |
| INTESTINE | 0.22 ± 0.02 | 0.21 ± 0.04 | 0.15 ± 0.02 |
| UTERUS | 0.36 ± 0.01 | 0.27 ± 0.03 | 0.26 ± 0.01 |
| TUMOR | 0.34 ± 0.03 | 0.35 ± 0.02 | 0.37 ± 0.01 |
| MUSCLE | 0.08 ± 0.00 | 0.05 ± 0.00 | 0.04 ± 0.01 |
| BONE | 0.37 ± 0.02 | 0.29 ± 0.02 | 0.29 ± 0.02 |
| BRAIN | 0.11 ± 0.01 | 0.05 ± 0.01 | 0.03 ± 0.01 |
| T/BLOOD | 0.01 ± 0.01 | 0.20 ± 0.02 | 0.33 ± 0.02 |
| T/MUSCLE | 4.43 ± 0.56 | 7.19 ± 0.56 | 9.82 ± 1.96 |

% of injected dose per gram of tissue weight (n = 3/time, interval, iv)
Value shown represent the mean ± standard deviation of data from 3 animals As shown in the above table 1, $^{99m}$Tc-GP-A still retained in rat's body at 4 hours after administration. Moreover, $^{99m}$Tc-GP-A especially accumulated at liver, spleen, kidney but decayed at blood and muscle. It is also noted that the accumulation of $^{99m}$Tc-GP-A in tumor tissue is also observed, which implies that if GP-A of the present invention is applied as a radioprotectant or chemoprotectant in a chemotherapy and/or radiation therapy for normal tissue, the administration thereof may be preferably after the exposing of chemotherapy and/or radiation therapy for minimizing effect on the therapy.

Nevertheless, the experimental result proves that the disclosed structure of GP-A can prolong the retention time of amifostine in most of the organs to at least 4 hours and is especially favorable for GP-A accumulation at important organs such as liver, spleen, kidney. Therefore, accompanying with the inherent radioprotection ability of amifostine, the GP-Amifostine structure of the present invention is expected to have the ability of reducing damage from free radicals in a more effective manner.

Figure 4A:
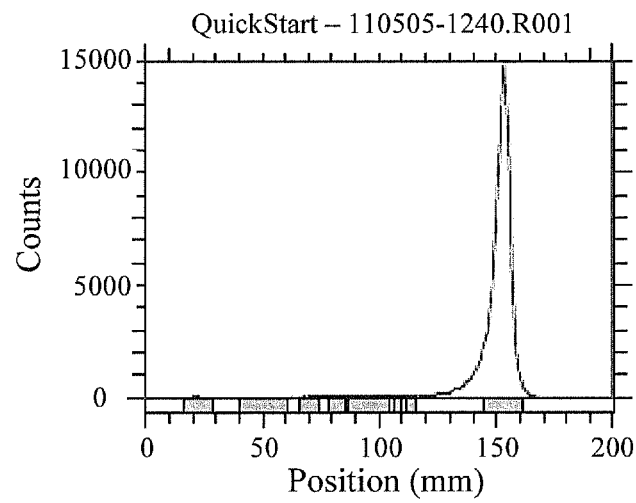
FIG. 4(*a*) and FIG. 4(*b*) shows that the high radiochemical purity of the product when $^{99m}$Tc was labeled on GP-Amifostine.
Figure 4B:
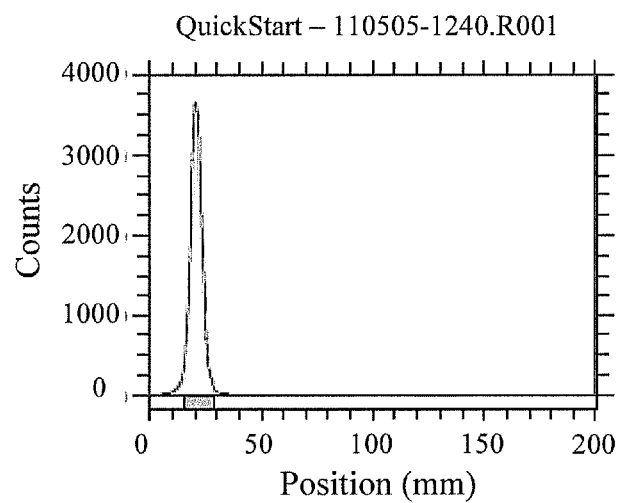

A supplementary experiment was also conducted to confirm the labeling of $^{99m}$Tc on GP-A was well-performed. As shown in both FIG. 4(a) and FIG. 4(b), $^{99m}$Tc was completely labeled with GP-A, and no free of $^{99m}$Tc was observed in FIG. 4(b). These two figures represent the high radiochemical purity of product when $^{99m}$Tc was labeled on GP-A, no other form of molecules are shown in this TLC assay. In other words, the aforesaid biodistribution data determined by detecting $^{99m}$Tc shall be reliable.

Example 4

Iodine Titration Experiment

According to the results of the above Example 3, we had demonstrated that GP-A of the present invention has the advantages of longer retention time and specific localization (accumulation). In this example, we would like to know that if modification of glycopeptides on Amifostine affects the inherent ability of quenching free radicals. An iodine titration experiment was conducted to examine the reducing power of amifostine and GP-amifostinel wherein the reducing power was considered as an indicator of the ability of quenching free radicals.

The iodine titration experiment was conducted based on the well-known protocol in this field. Briefly, amifostine and GP-amifostine were dissolved respectively in 0.9% of NaCl solution at various concentrations. The amifostine/NaCl solutions or GP-amifostine/NaCl solutions with different concentrations were mixed with a $CH_3COOH/CH_3COONa$ buffer system.

After mixing 1 mL of starch solution (1% v/v) with those amifostine/NaCl solutions or those GP-amifostine/NaCl solutions, titration was conducted with a 0.001 N of $I_2$ solution until permanent dark blue color showed.

Figure 2A:
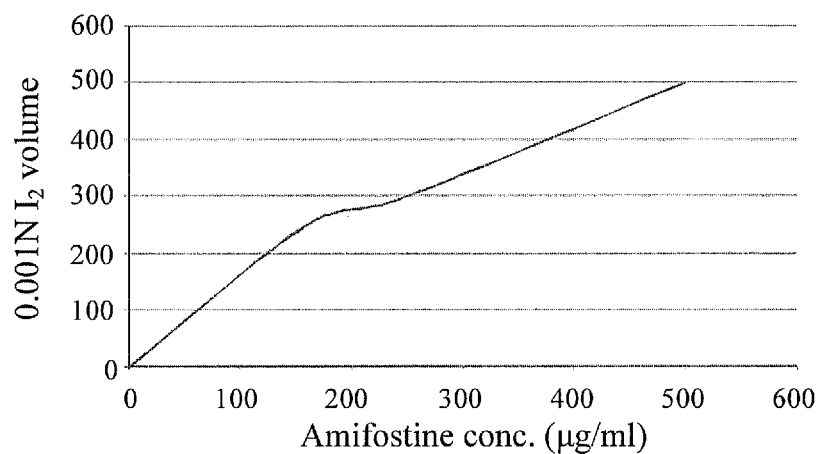
FIG. 2(*a*) and FIG. 2(*b*) show that the redox potential of Amifostine and GP-Amifostine respectively.
Figure 2B:
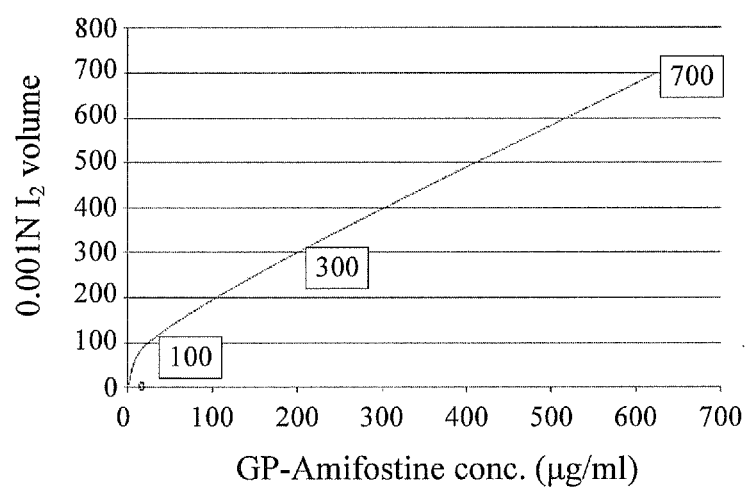

FIG. 2(a) and FIG. 2(b) show that the redox potential of amifostine and GP-Amifostine respectively. According to this result, the conjugation/modification of glycopeptides do not adversely affect the inherent ability of amifostine in quenching free radicals as the reducing power thereof is basically remained the same.

Example 5

Protection Ability Toward Plasmid DNA

In this example, we examined the ability of GP-A in protecting plasmid DNA from hydrogen peroxide ($H_2O_2$) and UV exposure, which was also an indicator of the ability of quenching free radicals because free radicals tend to attack DNA structure. Amifostine, GP-Amifostine and GP were respectively dissolved in dd-water at various concentrations. Nine experimental groups were conducted as shown in the following table 2:

TABLE 2

Experimental Condition of Example 5

| Lane | group | Experimental Condition |
|---|---|---|
| 1 | Experiment 1 (Control) | 2 μl pUC119 plasmid DNA solution + 8 μl dd-water |
| 2 | Experiment 2 (Negative Control) | 2 μl pUC119 plasmid DNA solution + 6.5 μl dd-water + 1 μl buffer + 0.5 μl EcoR I (incubated at 37° C. for one hour) |
| 3. | Experiment 3 | 2 μl pUC119 plasmid DNA solution + 3 μl dd-water + 3 μl $H_2O_2$ (with final concentration of 20 mM) + 20 $mJ/m^2$ UV exposure |
| 4. | Experiment 4 | 2 μl pUC119 plasmid DNA solution + 3 μl GP solution (4000 μg/ml) + 3 μl $H_2O_2$ (with final concentration of 20 mM) + 20 $mJ/m^2$ UV exposure |
| 5. | Experiment 5 | 2 μl pUC119 plasmid DNA solution + 3 μl Amifostine solution (2000 μg/ml) + 3 μl $H_2O_2$ (with final concentration of 20 mM) + 20 $mJ/m^2$ UV exposure |
| 6. | Experiment 6 | 2 μl pUC119 plasmid DNA solution + 3 μl GP-A soluion (4000 μg/ml) + 3 μl $H_2O_2$ (with final concentration of 20 mM) + 20 $mJ/m^2$ UV exposure |
| 7. | Experiment 7 | 2 μl pUC119 plasmid DNA solution + 3 μl mixture of GP(4000 μg/ml) and Amifostine (2000 μg/ml) + 3 μl $H_2O_2$ (with final concentration of 20 mM) + 20 $mJ/m^2$ UV exposure |
| 8. | Experiment 8 | 2 μl pUC119 plasmid DNA solution + 3 μl mixture of Amifostine solution (2000 μg/ml) and alkaline phosphatase (2 U/ml) + 3 μl $H_2O_2$ (with final concentration of 20 mM) + 20 $mJ/m^2$ UV exposure |
| 9. | Expriment 9 | 2 μl pUC119 plasmid DNA solution + 3 μl mixture of GP-A solution (4000 μg/ml) and alkaline phosphatase (2 U/ml) + 3 μl $H_2O_2$ (with final concentration of 20 mM) + 20 $mJ/m^2$ UV exposure |

The above-nine experimental groups were then mixed with 3 μl loading dye for electrophoresis in order to observe the integrity of the plasmid DNA.

Figure 3:
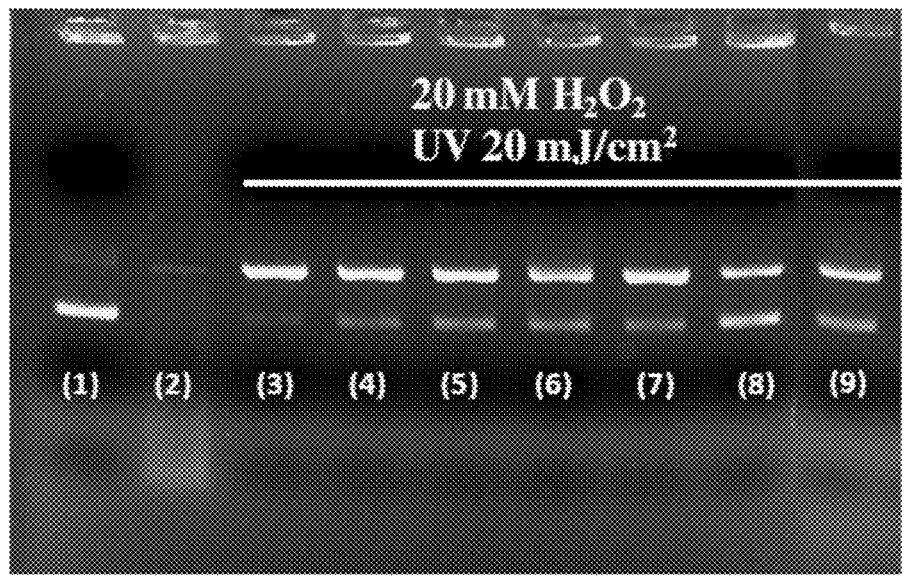
FIG. 3 shows the protection ability of Amifostine, GP-Amifostine, and GP against UV & $H_2O_2$ treated plasmid DNA.

FIG. 3 shows that both the Amifostine and GP-Amifostine have solid and slight protection ability against UV & $H_2O_2$ treated plasmid DNA. Based on the observation above (FIG. 2(a)、FIG. 2(b) and FIG. 3), it is confirmed that the protection ability of both Amifostine and GP-Amifostine of the present invention in blocking the transmission of free radical.

What is claimed is:

1. A pharmaceutical polymer, comprising:
    (a) a glycopeptide, having a polypeptide and a chitosan; wherein said chitosan is covalently bound to said polypeptide; and
    (b) an amifostine, having at least one amino group;
    wherein:
    said at least one amino group of said amifostine is covalently bound to said glycopeptide;
    wherein said polypeptide comprises poly(aspartic acid); and
    wherein said pharmaceutical polymer has a retention of at least 4 hours in a mammal.

2. The pharmaceutical polymer according to claim 1, wherein said chitosan covalently bonds to at least one carboxylic acid group of said polypeptide.

3. The pharmaceutical polymer according to claim 1, wherein said at least one amino group of said amifostine covalently bonds to at least one carboxylic acid group of said polypeptide.

4. The pharmaceutical polymer according to claim 1, wherein said pharmaceutical polymer has a molecular weight of 6,300 to 12,000 daltons.

5. The pharmaceutical polymer according to claim 1, wherein said chitosan has at least one amino group.

6. The pharmaceutical polymer according to claim 5, wherein said at least one amino group of said chitosan covalently bonds to at least one carboxylic acid group of said polypeptide.

7. A method for quenching free radicals, comprising administering an effective amount of the pharmaceutical polymer according to claim 1 to a subject.

8. The method according to claim 7, wherein said administering is via oral or intravenous injection.

9. The method according to claim 7, wherein said free radicals result from exposing said subject to radiation.

10. The method according to claim 9, wherein said administering is made before or after said exposing.

11. The method according to claim 9, wherein said radiation is x-ray radiation, nuclear radiation, gamma radiation, alpha radiation, beta radiation or a combination thereof.

12. The method according to claim 7, wherein said effective amount is 100~5,000 mg/m$^2$.

13. The method according to claim 7, wherein said subject is an animal.

14. The method according to claim 13, wherein said animal is human.

15. A pharmaceutical composition, comprising:
    a pharmaceutical polymer according to claim 1; and
    a pharmaceutical acceptable carrier.

16. The pharmaceutical composition according to claim 15, wherein said pharmaceutical acceptable carrier comprises glucose, saccharose, lactose, fructose, starch, dextrins, cyclodextrins, polyvinylpyrrolidone, alginic acid, tylose, silicic acid, cellulose, cellulose derivatives, mannitol, sorbitol, calcium carbonate, calcium phosphate, or any combination thereof.

\* \* \* \* \*